United States Patent
Mori et al.

(10) Patent No.: US 6,897,300 B1
(45) Date of Patent: May 24, 2005

(54) NICOTIANAMINE AMINOTRANSFERASE AND GENE THEREFOR

(75) Inventors: Satoshi Mori, Narashino (JP); Hiromi Nakanishi, Tokyo (JP); Michiko Takahashi, Utsunomiya (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/026,400

(22) Filed: Feb. 19, 1998

(30) Foreign Application Priority Data

Feb. 21, 1997 (JP) .............................. 9-037499

(51) Int. Cl.⁷ ............................. C12N 1/00; C12N 5/04; C12N 15/29; C12N 15/52; C12N 15/82
(52) U.S. Cl. .................... 536/23.6; 536/23.1; 536/23.2; 435/243; 435/320.1; 435/419; 435/468
(58) Field of Search ................................ 800/278, 298, 800/320, 317.3, 290, 295; 536/23.1, 23.2, 23.6; 435/419, 230.1, 243, 468, 320.1, 69.1, 466, 410

(56) References Cited

PUBLICATIONS

Shojima et al., Plant Cell Physiol., vol. 30, No. 5, pp. 673–677 (1989).
Shojima et al., Plant Physiol., vol. 93, pp. 1497–1503 (1990).
Ohata et al., Soil Sci. Plant Nutr., vol. 39, No. 4, pp. 745–749 (1993).
Kanazawa et al., J. Exper. Botany, vol. 45, No. 281, pp. 1903–1906 (Dec. 1994).
Kanazawa et al., J. Abadia (ed.) Iron Nutrition in Soils and Plants, pp. 37–41 (1995).
Kanazawa et al., J. Exper. Botany, vol. 46, No. 290, pp. 1241–1244 (Sep. 1995).
Takahashi et al., Abstr. Paper of Meeting of Japanese Society of Plant Physiologists, Kyoto University, Japan Mar. 27–29, 1997 (English translation).
Takahashi et al., Abstr. Paper of Meeting of Japanese Society of Soil Science and Plant Nutrition, Shizuoka, Japan Apr. 2–4, 1997 (English translation).
Takahashi et al., Abstr. Paper of 9$^{th}$ Int'l. Symposium on Iron Nutrition and Interactions in Plants, Hohenheim University, Germany, Jul. 20–25, 1997.
Takahashi et al., Abstr. Paper of XIII Int'l. Plant Nutrition Colloquium, Tokyo, Japan, Sept. 13–19, 1997.
S. Mori, Soil Sci. Plant Nutr., vol. 43, pps. 975–980, (1997).
M. Takahashi et al., Plant nutrition for sustainable food production and environment. T. Ando eds. Kluwer Academic Press. Doordrecht. pp. 279–280, (1997).

*Primary Examiner*—Phuong T. Bui
*Assistant Examiner*—Russell Kallis
(74) *Attorney, Agent, or Firm*—Birch, Stewart, Kolasch & Birch, LLP

(57) ABSTRACT

A protein having an amino acid sequence represented by SEQ ID NO: 1 or 2 or an amino acid sequence having said amino acid sequence with a single or plural amino acids deleted, replaced or added, and having the nicotianamine aminotransferase activity, a gene encoding said protein as well as utilization thereof for enhancement of ability of absorbing insoluble iron in soil and for improvement of resistance to iron deficiency are provided.

15 Claims, No Drawings

NICOTIANAMINE AMINOTRANSFERASE AND GENE THEREFOR

BACKGROUND OF THE INVENTION

1. Field of the Invention

The present invention relates to a nicotianamine aminotransferase, a gene therefor and utilization thereof.

2. Description of Related Art

Calcareous soil, a saline illuviation soil in dry ground, occupies about 30% of the soil in the world, including China, the Middle and Near East countries, the Central and North Africa, the Central and West America and soon. In this soil, iron in the soil is insolubilized due to a high pH. A plant can not grow in this soil, developing chlorosis by iron deficiency, unless it can absorb iron in soluble form from the root by any means. When agriculture and environmental afforestation are desired, measures against the deficiency of soluble iron in the soil will be an important problem.

As measures to solve the iron deficiency of plant by agricultural technique, it may be considered (1) to correct pH of the alkaline soil to neutral or slightly acidic one by addition of sulfur, (2) to apply a substance containing a chelated iron or (3) to increase soluble iron in the soil by enhancing soil microorganism activity, for example, by means of application of an organic substance, thereby increasing siderophore (an iron transporter) production by the microorganism.

These means for providing iron by soil treatment, however, are not always satisfactory because there are problems, for example, that a large amount of application material is required, that the effect is very unstable depending on the method of application including time of application, site of application, concentration, kind of spreader or the like and weather conditions. Therefore, development of novel techniques has been demanded.

Under these circumstances, the present inventors have conducted extensive studies and discovered a novel gene which is suitable for enhancing absorption ability on insoluble iron in soil and improving resistance to iron deficiency and thus have completed the present invention.

SUMMARY OF THE INVENTION

Accordingly, the present invention provides:

(1) A protein comprising an amino acid sequence represented by SEQ ID NO: (2 or 4) or an amino acid sequence having said amino acid sequence with a single or plural amino acids deleted, replaced or added, and having the nicotianamine aminotransferase activity (hereinafter, referred to as the protein of the present invention), (2) A gene encoding the protein as defined in the foregoing item 1 (hereinafter, referred to as the gene of the present invention), (3) The gene in accordance with the foregoing item 2 having a nucleotide sequence encoding the amino acid sequence represented by SEQ ID NO: 2 or 4, (4) The gene in accordance with the foregoing item 3 having a nucleotide sequence represented by SEQ ID NO: 1 or 3, (5) A plasmid comprising the gene in accordance with the foregoing item 2 (hereinafter, referred to as the plasmid of the present invention), (6) An expression plasmid comprising (1) a promoter capable of functioning in a host cell, (2) the gene in accordance with the foregoing item 2 and (3) a terminator capable of functioning in a host cell, operably linked in the above described order (hereinafter, referred to as the expression plasmid of the present invention), (7) A process for constructing an expression plasmid, which comprises combining (1) a promoter capable of functioning in a host cell, (2) the gene in accordance with the foregoing item 2 and (3) a terminator capable of functioning in a host cell, operably linked in the above described order (hereinafter, referred to as the process for construction of the present invention),, (8) A transformant comprising a host cell harboring the plasmid as defined in foregoing item 5 or 6, (9) The transformant in accordance with the foregoing item 8, wherein the host is a microorganism.

(10) The transformant in accordance with the foregoing item 8, wherein the host cell is a plant cell,

(11) A process for enhancing iron absorbing ability of a host cell, which comprises introducing into a host cell an expression plasmid formed by combining (1) a promoter capable of functioning in a host cell, (2) a nicotianamine aminotransferase gene and (3) a terminator capable of functioning in a host cell, operably linked in the above described order and transforming said host cell,

(12) The process in accordance with the foregoing stem 11, wherein the host cell is a plant cell,

(13) The process in accordance with the foregoing item 12, wherein the gene of the nicotianamine aminotransferase is the gene as defined in the foregoing item 2,

(14) A gene fragment having a partial sequence of the gene in accordance with the foregoing item 2, 3 or 4 (hereinafter, referred to as the gene fragment of the present invention),

(15) The gene fragment in accordance with the foregoing item 14, wherein the number of the base is 15 or more and 50 or less,

(16) The gene fragment in accordance with the foregoing item 14 having the nucleotide sequence represented by SEQ ID NO: 5 or 6,

(17) A process for detecting a nicotianamine aminotransferase gene, which comprises detecting from plant gene fragments a nicotianamine aminotransferase gene having ri a nucleotide sequence encoding an amino acid sequence of an enzyme with the nicotianamine aminotransferase activity or a gene fragment thereof by applying the hybridization method using the gene fragment in accordance with the foregoing item 14, 15 or 16 (hereinafter, referred to as the process for detection of the present invention),

(18) A process for amplifying a nicotianamine aminotransferase gene, which comprises amplifying a nicotianamine aminotransferase gene having a nucleotide sequence encoding an amino acid sequence of an enzyme with the nicotianamine aminotransferase activity or a gene fragment thereof by applying PCR (polymerase chain reaction) on a plant gene fragment using the gene fragment as defined in the foregoing item 14, 15 or 16 as a primer (hereinafter, referred to as the process for amplification of the present invention),

(19) A process for obtaining a nicotianamine aminotransferase gene, which comprises identifying a nicotianamine aminotransferase gene or a gene fragment thereof by the process as defined in the foregoing item 17 or 18, and isolating and purifying the identified gene or the gene fragment thereof, and

(20) A nicotianamine aminotransferase gene obtained by the process as defined in the foregoing item 19.

DETAILED DESCRIPTION OF THE INVENTION

The present invention will be described below in more detail.

The protein of the present invention comprises the amino acid sequence represented by SEQ ID NO: 2 or 4 or an amino acid sequence having said amino acid sequence with a single or plural amino acids deleted, replaced or added, and having the nicotianamine aminotransferase activity.

Such protein can be prepared from Gramineae plants, for example, barley (*Hordeum vulgare*) or the like by a process, for example, a process described below.

Examples of the protein of the present invention include an amino acid sequence of SEQ ID NO: 1 or 2 or an amino acid sequence having a molecular weight of 47 kDa comprising 429 amino acids beginning from the amino acid of NO: 33 in SEQ ID NO: 2.

The nicotianamine aminotransferase activity hereinafter refers to an ability of transferring an amino group from nicotianamine to 2-oxoglutarate.

The nicotianamine aminotransferase activity can be measured by, for example, a method described in Kanazawa, K et al., Journal of Experimental Botany, 45, 1903–1906 (1994) and others. Specifically, substrates nicotianamine, 2-oxoglutaric acid, and pyridoxal phosphate as a coenzyme are added to an enzyme solution and the mixture is reacted at 25° C. for 30 minutes. After the reaction, the reaction product is reduced by adding NaBH$_3$ and deoxymugineic acid is determined by HPLC.

In order to prepare the protein of the present invention from a Gramineae plant such as barley (*Hordeum vulgare*) or the like, for example, whole root of a Gramineae plant such as barley or the like treated for iron deficiency is triturated and the protein of the present invention is partly purified by subjecting the obtained extract to hydrophobic interaction chromatography, adsorption chromatography, anion exchange chromatography, gel filtration, and second adsorption chromatography in this order using the activity as an indicator. The individual protein fraction obtained from the second adsorption chromatography is subjected to two-dimensional electrophoresis and protein spots are detected which rises and falls in proportion to the intensity of nicotianamine aminotransferase activity of each fraction. The detected spots indicate the protein of the present invention. The protein of the present invention can be purified by isolating from the two-dimensional electrophoresis gel.

Mugineic acid analogues such as deoxymugineic acid produced by a reaction catalyzed by the protein of the present invention and a subsequent reduction reaction, mugineic acid and 3'-hydroxymugineic acid produced by a still subsequent hydroxylation reaction, or the like, solubilizes iron by forming a chelate complex with insoluble iron in the soil. Some kind of plants can biosynthesize said mugineic acid analogues, which are secreted from their root to the soil in the rooting zone, thereby solubilizing insoluble iron in the form of a mugineic acid complex and absorbing the iron complex directly through the root. Therefore, it is possible to enhance production of mugineic acid analogues and increase ability of absorbing insoluble iron by appropriately expressing a large amount of the protein of the present invention in said plants.

The gene of the present invention encodes a protein comprising the amino acid sequence represented by SEQ ID NO: 2 or 4 or an amino acid sequence having said amino acid sequence with a single or plural amino acids deleted, replaced or added, and having the nicotianamine aminotransferase activity.

Such gene can be prepared from Gramineae plants, for example, barley (*Hordeum vulgare*) or the like by a process, for example, a process described below.

Further, the gene of the present invention includes a gene encoding a protein comprising the amino acid sequence represented by SEQ ID NO: 2 or 4 or an amino acid sequence having said amino acid sequence with a single or plural amino acids deleted, replaced or added, and having the nicotianamine aminotransferase activity and encompasses a gene, for example, that hybridizes with the said gene sequence under stringent conditions. The stringent conditions herein refer to conditions used, for example, in the screening of cDNA library described in Example 4.

Specific examples of the nucleotide sequence of the gene include the nucleotide sequence represented by SEQ ID NO: 1 (the loci of CDS being 62-1444) or SEQ ID NO: 2 (the loci of CDS being 76-1731).

It is possible to increase ability of absorbing insoluble iron in the soil in the rooting zone and improve resistance to iron deficiency by introducing the gene of the present invention into a plant which absorbs iron making use of mugineic acid compounds thereby enhancing biosynthesizing ability of mugineic acid compounds in the obtained transformant plant.

In order to prepare the gene of the present invention, for example, the amino acid sequence of peptide fragments obtained by partially hydrolyzing the protein of the present invention and the N-terminal amino acid sequence of the protein of the present invention are determined by a protein sequencer. Two or more primers comprising DNA sequences expected from these amino acid sequences are synthesized. By conducting PCR using as a template a cDNA synthesized from mRNA prepared from the root of a Gramineae plant such as barley treated for iron deficiency by means of a reverse transcriptase, cDNA fragment of the gene of the present invention is amplified. Using the amplified cDNA fragment as a probe, screening of cDNA library described below is performed. A cDNA is synthesized from mRNA prepared from the root of a Gramineae plant such as barley treated for iron deficiency by means of a reverse transcriptase and this is integrated into a phage vector such as lambda ZAPII or the like or a plasmid vector such as pUC or the like to prepare a cDNA library. This library is screened using the above-mentioned probe and a cDNA of the nicotianamine aminotransferase gene is selected. The selected cDNA can be confirmed to be that of the nicotianamine aminotransferase gene (cDNA of the gene of the present invention) by determining the sequence of the selected cDNA.

In order to obtain genome DNA using the cDNA selected in this manner and determine its sequence, for example, plant tissue such as leaf, stem, root or the like is instantly frozen and sufficiently triturated with a mortar and pestle or a Waring blender. The genome DNA is extracted from the obtained triturated product according to the ordinary method as described in Itaru Watanabe (supervisor), Masahiro Sugiura (editor), "Cloning and Sequencing (a manual for experiment of plant biotechnology)", Nosonbunka-sha, Tokyo (1989) or the like. The obtained genome DNA is digested with an appropriate restriction enzyme and the obtained genome DNA fragments are fractionated by a known method such as sucrose density gradient centrifugation or cesium chloride equilibrium centrifugation or the like. Each of the genome DNA fragment fractions is subjected to normal Southern hybridization using the selected cDNA (cDNA of the gene of the present invention) as a probe to decide a genome DNA fragment fraction containing the desired gene.

A genome DNA library is prepared by ligating the genome DNA fragment fraction to a commercially available vector such as plasmid, phage, cosmid or the like. The library is subjected to normal screening by hybridization using the cDNA of the gene of the present invention as a probe to obtain a genome DNA clone containing a nucleotide sequence encoding the amino acid sequence of the protein of the present invention. The obtained DNA clone can be subcloned to a vector, for example, plasmid or the like suitable for analysis of gene sequence and the sequence is analyzed according to a routine method to determine the sequence of the genome DNA containing a sequence encoding the amino acid sequence of the protein of the present invention.

The transcription initiation site of genome DNA of the gene of the present invention can be determined by the primer extension method described in Bina-Stem, Met et al., Proc. Natl. Acad. Sci. USA, 76, 731 (1979), Sollner-Webb and Reeder, R. H., cell, 18, 485 (1979) or the like or the Si mapping method described in Berk, A. J. and Sharp, P. A., Proc. Natl. Acad. Sci. USA, 75, 1274 (1978). A TATA sequence necessary for the transcription initiation is present in the upstream of the transcription initiation site decided in this manner. A promoter sequence bearing control of gene expression is present usually at 1 kb to about 10 kb upstream of this transcription initiation site. The promoter region of the gene of the present invention can be finally determined, for example, by connecting gene fragments having promoter regions of various length with a reporter gene such as GUS or the like, preparing transgenic plants into which the connected product are introduced, and studying presence or absence of expression of the reporter gene in various tissues of the prepared plants.

On the other hand, a terminator sequence is present in the genome DNA region corresponding to a poly-A sequence usually present in the downstream of a poly-(A) addition signal (consensus sequence being AATAAA) which exists in a terminal 3'-nontranslation region at the downstream of termination codon, and has an effective translation terminating function.

The plasmid of the present invention contains a gene encoding a protein comprising the amino acid sequence represented by SEQ ID NO: 2 or 4 or an amino acid sequence having said amino acid sequence with a single or plural amino acids deleted, replaced or added, and having the nicotianamine aminotransferase activity.

Preferred specific examples of the plasmid include a plasmid prepared by cloning a nicotianamine aminotransferase gene having a nucleotide sequence encoding the amino acid sequence represented by SEQ ID NO: 1 into pSK– (Strategene). This has a characteristic that its vector portion is small, it has a great number of copies in *Escherichia coli*, and thus it is suitable for preparation of DNA or analysis of DNA structure.

The expression plasmid of the present invention can be constructed by combining (1) a promoter capable of functioning in a host cell, (2) the gene encoding a protein comprising the amino acid sequence represented by SEQ ID NO: 2 or 4 or an amino acid sequence having said amino acid sequence with a single or plural amino acids deleted, replaced or added, and having the nicotianamine aminotransferase activity and (3) a terminator capable of functioning in a host cell, operably linked in the above described order.

The expression "operably linked" used hereinafter means that, when the constructed plasmid is introduced into a host cell to transform it, the gene of the present invention is integrated under the control of a promoter such that the gene has a function of expressing the protein of the present invention in said host cell.

The promoter capable of functioning in a host cell includes, for example, *Escherichia coli* lactose operon promoter, yeast alcohol dehydrogenase (ADH) promoter, adenovirus major late (Ad. ML) promoter, SV40 early promoter, baculovirus promoter and the like. When the host cell is a plant cell, the promoter includes, for example, T-DNA derived constitutive promoters such as nopaline synthase gene (NOS) promoter, octopine synthase gene (OCS) promoter and the like, plant virus derived promoters such as cauliflower mosaic virus (CaMV) derived 19S and 35S promoters and the like, and inducible promoters such as phenylalanine ammonialyase (PAL) gene promoter, chalcone synthase (CHS) gene promoter, pathogen-related (PR) gene promoter and the like. Further, it includes known plant promoters not limited to them.

The terminator capable of functioning in a host cell includes, for example, yeast HIS terminator sequence, ADH1 terminator, SV40 early splicing region and the like. When the host cell is a plant cell, the terminator includes, for example, T-DNA derived constitutive terminators such as nopaline synthase gene (NOS) terminator and the like, plant virus derived terminators such as garlic virus GV1, GV2 terminators and the like. Further, it includes known plant terminators not limited to them.

A host cell is transformed by introducing such plasmid ((expression) plasmid of the present invention) into said host cell. When the host cell is a plant cell, the (expression) plasmid of the present invention is introduced into a plant cell by any of conventional means such as *Agrobacterium* infection method (JP-B-2-58917 and JP-A-60-70080), electroporation method into protoplast (JP-A-60-251887 and JP-A-5-68575), particle gun method (JP-A-508316 and JP-A-63-258525) and the like, and a transformed plant cell can be obtained by selecting a plant cell into which the gene of the present invention is introduced. The transformed plant body is obtained by regenerating a plant body according to a conventional plant cell culturing process, for example, described in Hirohumi Utimiya, Manual for Plant Gene Manipulation (Method for Producing Transgenic Plants), Published by Kodansha Scientific (ISBN4-06-153515-7 C3045), 1990, pages 27–55.

By introducing the plasmid of the present invention into host cells which are any kind of microorganism such as *Escherichia coli* or the like and allowing high expression in said host cells, a large amount of the protein of the present invention can easily be isolated from the host cells A screening system for inhibitors to nicotianamine aminotransferase activity constructed by utilizing the mass produced protein of the present invention. For example, according to the process for measuring nicotianamine aminotransferase activity described above, substrates nicotianamine, 2-oxoglutaric acid and pyridoxal phosphate as the coenzyme as well as a candidate inhibitor compound are added to the prepared enzyme solution, and the mixture is reacted at 25° C. for 30 minutes. After the reaction, compounds showing no nicotianamine aminotransferase activity are selected by reducing the reaction product with addition of $NaBH_3$ and deoxymugineic acid by HPLC.

In plants absorbing iron utilizing mugineic acid compounds, expression of the nicotianamine aminotransferase gene is strongly induced in iron deficiency conditions. Since the common soil (upland soil) is under the oxidative conditions and the ferric iron concentration in soil solution is only a level extremely lower than $10^{-4}$–$10^{-8}$ M that is required by plants, nicotianamine aminotransferase gene and mugineic acid biosynthesis gene are always strongly induced. In other words, plants positively absorb insoluble iron by routinely biosynthesizing mugineic acid compounds and secreting them from the root to the soil in the rooting zone.

The inhibitors to nicotianamine aminotransferase activity selected by the screening system may be compounds useful as selective herbicides against plants that absorb iron by utilizing compounds analogous to mugineic acid.

Further, the present invention provides a process for enhancing iron absorbing ability, which comprises introducing in a host cell an expression plasmid formed by combining (1) a promoter capable of functioning in a host cell, (2) a nicotianamine aminotransferase gene and (3) a terminator capable of functioning in a host cell, operably in the above described order and transforming said host cell. The promoter capable of functioning in a host cell includes the promoters as described above.

The nicotianamine aminotransferase gene includes, for example, a plant derived nicotianamine aminotransferase gene and preferably the gene of the present invention.

The terminator capable of functioning in a host cell includes the terminators as described above.

The gene fragment of the present invention refers to a gene fragment having a partial sequence of the gene of the present invention represented by SEQ ID NO: 1 or 3 and includes a gene fragment having a partial sequence of the gene encoding a protein comprising the amino acid sequence represented by SEQ ID NO: 2 or 4 or an amino acid sequence having said amino acid sequence with a single or plural amino acids deleted, replaced or added, and having the nicotianamine aminotransferase activity, specifically, for example, a gene fragment represented by SEQ ID NO: 5 or 6.

These gene fragments are useful as probes in hybridization or primers in PCR. Particularly, as primers used in PCR, a gene fragment having 15 or more and 50 or less nucleotides are preferred.

The process for detection of the present invention is a process in which a nicotianamine aminotransferase gene having a nucleotide sequence encoding an amino acid sequence of an enzyme with the nicotianamine aminotransferase activity or a gene fragment thereof is detected from plant gene fragments by applying the hybridization method using the gene fragment of the present invention as a probe.

Specifically, for example, the process can be all performed according to the method described in "Molecular Cloning: A Laboratory Manual, 2nd edition" (1989), Cold spring Harbor Laboratory Press or in "Current Protocols in Molecular Biology" (1987), John Wiley & Sons, Inc., ISBN0-471-50338-X. The gene fragments used here may include, for example, cDNA library, genome DNA library or the like of the targeted plant. Said plant gene fragments may be a commercially available library as such derived from a plant, or may also be a library prepared according to the conventional method for preparing a library described in "Molecular Cloning: A Laboratory Manual, 2nd edition" (1989), Cold Spring Harbor Laboratory Press or in "Current Protocols in Molecular Biology" (1987), John Wiley & Sons, Inc., It can also be possible to obtain nicotianamine aminotransferase gene by identifying the nicotianamine aminotransferase gene or a fragment thereof according to the process for detection of the present invention and isolating/purifying the identified gene or gene fragment.

The process for detection of the present invention may be utilized in analysis of plants. Specifically, a plant genome DNA is prepared from different cultivars of a specific plant species according to the process for detection of the present invention the ordinary method described in Itaru Watanabe (supervisor), Masahiro Sugiura (editor), "Cloning and Sequencing (a manual for experiment of plant biotechnology)", Nosonbunka-sha, Tokyo (1989) or the like. It is then incised with at least several kinds of suitable restriction enzymes, electrophoresed, and used for preparing a filter by brotting according to the ordinary method.

Hybridization is conducted on the filter using a probe prepared by the ordinary method and differences in phenotype character accompanied by mugineic acid biosynthesis between cultivars based on the difference in length of DNA fragments. Further, a plant is decided to be a recombinant gene plant if the plant has a greater number of detected hybridization bands than a non-recombinant gene plant when the specific plant is compared with the non-recombinant plant. This method is preferably carried out according to the RFLP (Restriction Fragment Length Polymorphism) method described in Ko Shimamoto and Takuji Sasaki (supervisors), "Protocols for PCR Experiment on Plants", Shujunsha, Tokyo (1995), ISBN4-87962-144-7, pp 90–94.

The process for amplification of the present invention is a process in which a nicotianamine aminotransferase gene having a nucleotide sequence encoding an amino acid sequence of an enzyme with the nicotianamine aminotransferase activity or a gene fragment thereof is amplified by applying PCR (polymerase chain reaction) on a plant gene fragments using the gene fragment of the present invention as a primer. Specifically, for example, the process can be performed according to the method described in Ko Shimamoto and Takuji Sasaki (supervisors), "Protocols for PCR Experiment on Plants", Shujunsha, Tokyo (1995), ISBN4-87962-144-7 or the like.

It can also be possible to obtain nicotianamine aminotransferase gene by identifying the nicotianamine aminotransferase gene or a fragment thereof according to the process for amplification of the present invention and isolating/purifying the identified gene or gene fragment.

Further, the process for amplification of the present invention may be utilized in analysis of plants. Specifically, for example, a part or the whole of the gene of the present invention is amplified by conducting PCR using a plant genome DNA prepared from a specific plant species as a template and the gene fragment of the present invention as a primer. The obtained PCR product is mixed with a formaldehyde solution and the mixture is denatured by heating at 85° C. for 5 minutes, followed by rapid cooling on ice. This sample is electrophoresed on, for example, 6% acrylamide gel containing glycerol at a concentration of 0% or 10%. The electrophoresis is carried out with a commercially available electrophoresis apparatus for SSCP (Single Strand Conformation Polymorphism) keeping the gel temperature at, for example, 5° C., 25° C., 37° C. and so on. The migrated gel is subjected to ethidium bromide staining or the like using a commercially available reagent to detect DNA.

Differences in phenotype character accompanied by mugineic acid biosynthesis between cultivars based on mutation in the gene of the present invention is analyzed from the differences in migration of the DMA fragments detected. This method is preferably carried out according to the method described in Ko Shimamoto and Takuji Sasaki (supervisors), "Protocols for PCR Experiment on Plants", Shujunsha, Tokyo (1995), ISBN4-87962-144-7, pp 141–146.

EXAMPLES

The present invention will now be described in more detail on the bases of Examples, which should not be construed as a limitation upon the scope of the present invention.

Example 1

Method of Isolating the Protein of the Present Invention

In an extraction buffer solution (0.2 M Tris-HCl, 10 mM EDTA, 0.1 mM p-APMSF, 10 mM DTT, 5% glycerol, 5% polyvinyl pyrrolidone, pH 8.) was triturated 150 g of root of barley treated for iron deficiency. The trituration product was centrifuged at 8,000×g for 30 minutes and the supernatant was separated. Ammonium sulfate was added to the obtained supernatant until 30% saturation was attained. The produced sample was applied over Butyl Toyopearl (manufactured by Toso) equilibrated with 30% saturated ammonium sulfate buffer (50 mM Tris-HCl (pH 8.0), 5 mM EDTA, 10 mM DTT), and eluted with 15% saturated ammonium sulfate buffer after washing with the former buffer. To eluted fractions was added p-APMSF at a final concentration of 0.1 mM and the mixture was dialyzed overnight against 0.1 mM KCl, 50 mM $KH_2PO_4/K_2HPO$, (pH 6.8), 10 mM DTT, followed by application over Hydroxylapatite (100–350 mesh, manufactured by Nakarai) equilibrated with said buffer. Then it was washed with the same buffer and eluted with 0.5 M $KH_2PO_4/K_2HPO$, (pH 6.8), 10 mM DTT. The eluted fractions were treated with Molecut (Millipore, differential molecular weight 10,000) in order to exchange buffer with 20 mM Tris-HCl (pH 8.0), 10 mM KCl, 10 mM DTT and applied over DEAE Sephasel (manufactured by Pharmacia) equilibrated with the same buffer. After washing with the same buffer, it was eluted with 10 mM –500 mM KCl concentration gradient. Non-adsorbed fractions from DEAE Sephasel were treated with Molcut in order to exchange buffer with 20 mM Tris-HCl (pH 8.0), 10 mM KCl, 5 mM EDTA, 1 mM DTT and applied over NA-Sepharose 4B which was EAH-Sepharose 4B (manufactured by Pharmacia) having bound nicotianamine (NA). After washing with the same buffer, it was eluted with 1 mM NA, 10 mM KCl, 20 mM Tris-HCl (pH 6.0). The eluted fractions were subjected to two-dimensional electrophoresis, which allowed very concentrated spot as compared with the sample before applying on NA-Sepharose 4B column. The spot indicated the protein of the present invention, which was isolated by separating said spot.

The N-terminal amino acid sequence of the protein of the present invention as separated was analyzed by a protein sequencer (manufactured by Applied Biosystems). The result showed revealed an amino acid sequence shown by the amino acids of Nos. 33 to 47 in the Seq. ID NO.1. Further, N-terminal amino acid sequences for 3 peptide fragments formed by treating it with 70% formic acid solution containing 1% bromocyan were analyzed in the same manner.

Example 2

Preparation of a Probe for Cloning of cDNA of the Protein of the Present Invention From 6 g of root of barley treated for iron deficiency 255 μg of whole RNA was recovered according to the SDS-phenol method described in Itaru Watanabe (supervisor), Masahiro Sugiura (editor), "Cloning and Sequencing (a manual for experiment of plant biotechnology)", Nosonbunka-sha, Tokyo (1989), pp 34–40. From the recovered whole RNA, 75 μg portion was taken and used to prepare poly(A)+RNA using Dynabeads mRNA Purification Kit (manufactured by Dynal). The prepared poly(A)+RNA was reverse transcribed with dT17 adapter primer (5'-GACTCGAGTCGACATCGATTTTTTTTTTTTTTTTT-3' (SEQ ID NO: 7)) to prepare cDNA. A part of the prepared cDNA was used for amplification of cDNA fragment of the gene of the present invention by two steps PCR. In the first reaction, PCR was conducted with a primer 1 (5'-GCIGTIGARTGGAAYTTYGCIMG-3' (SEQ ID NO: 5)) synthesized on the basis of N-terminal amino acid sequence of the protein of the present invention and the above described dT17 adapter primer and using the obtained cDNA as a template at 94° C. (40 seconds), 40° C. (1 minute), and 72° C. (2 minutes), repeated by 25 cycles, and at 94° C. (40 seconds), 45° C. (1 minute), and 72° C. (2 minutes), repeated by 25 cycles. Using this PCR reaction solution as a template, the second PCR was conducted with a primer 2 (5'-GCDATRTGICCRAAIACICC-3' SEQ ID NO: 6)) synthesized on the basis of N-terminal amino acid sequence of the peptide fragment formed by treating with 70% formic acid solution containing 1% bromocyan as described above and the primer 1 at 94° C. (40 seconds), 45° C. (1 minute), and 72° C. (2 minutes), repeated by 40 cycles. The DNA fragment of about 600 bp amplified by the second PCR was purified by excising from 0.8% agarose electrophoresis gel and used as a probe for screening cDNA library.

Example 3

Preparation of cDNA Library from Root of Barley Treated for Iron Deficiency

Using a commercially available cDNA synthesis kit (Super Script (trademark) Plasmid System for cDNA Synthesis and Plasmid Cloning, manufactured by Gibco BRL), cDNA was synthesized from 5 μg of poly(A)+RNA prepared from root of barley treated for iron deficiency described in Example 2. The product was ligated with SalI adapter and incised with NotI to recover cDNA.

A vector for cDNA library (hereinafter, referred to as pYH23) was prepared by adding some modification to yeast multi-copy plasmid YEplac181 described in R. Daniel Gietz and Akio Sugino, Gene, 74 (1988), pp 527–534. Specifically, HindIII and BamHI to EcORI site in the multi-cloning site of YEplac181 was eliminated. Further, promoter and terminator sequences of alcohol dehydrogenase derived from pTV-100 were subcloned at SphI site, and NotI linker was inserted at BamHI site of this fragment.

The pYH23 prepared in this manner was digested with NotI and XhoI, after inserting cDNA prepared as above,

*Escherichia coli* XLoI-Blue strain was transformed to provide cDNA library derived from 300,000 independent colonies.

Example 4

Screening of cDNA Clones of the Present Invention

A probe DNA for cDNA cloning of the protein of the present invention was prepared by radioactively labeling the probe prepared in Example 3 with a commercially obtainable radioactivity label kit (Random Primer DNA Labeling Kit Ver 2, TaKaRa). *Escherichia coli* having a plasmid DNA of cDNA library derived from root of barley treated for iron deficiency as prepared in Example 3 was inoculated in LB medium, incubated at 37° C. for 10 hours, and then transferred to a commercially available Nylon membrane (Hybond (trademark)-N+, Amersham Life Science). The membrane was treated with 10% SDS for 3 minutes, an alkaline denaturation solution (0.5 M NaOH, 1.5M NaCl) for 5 minutes, a neutralizing solution (0.5 M Tris-HCl (pH 7.0), 1.5 M NaCl) for 3 minutes, 2×SSPE (20 mM phosphate buffer (pH 7.4), 0.3 M NaCl, 5 mM EDTA) twice for 3 minutes, dried, and irradiated with ultraviolet rays for 3 minutes to irreversibly fix DNA on the membrane. Prehybridization was carried out at 65° C. for 1 hour using a prehybridization solution (5× Denhart's solution, 5×SSPE, 0.1% SDS, 100 µg/ml denatured salmon testis DNA). Then, hybridization was carried out in a solution having the radioactively labeled probe added to a hybridization solution (5× Denhart's solution, 5×SSPE, 0.1% SDS) at 65° C. for 12 hours. Thereafter, the membrane was washed once with 6×SSPE at 65° C. for 10 minutes, twice with 2×SSPE, 0.1% SDS at 42° C. for 10 minutes, and exposed to Fuji Medical X-ray Film to detect positive colonies. Second and third screenings were performed in the same manner and cDNA clone of the protein of the present invention was isolated.

Example 5

Determination of Nuceotide Sequence of cDNA Encoding the Protein of the Present Invention The cDNA clone of the protein of the present invention isolated in Example 4 was subcloned in a plasmid vector pBluescript SK(−) according to the conventional method described in J. Sambrook, E. F. Fritsh, T. Maniatis, "Molecular Cloning, Second Edition" Cold Spring Harbor Press (1989) to give a plasmid cDNA clone. Nucleotide sequence (SEQ. ID NO. 1 or 3) of the insert in said cDNA clone was determined (1) by 373A DNA Sequencer manufactured by Applied Biosystems using Taq Dye Primer Cycle Sequencing Kit (manufactured by Applied Biosystems), (2) by DSQ-1000L DNA Sequencer (manufactured by Shimadzu) using Thermo Sequence Fluorescent Labeled Primer Cycle Sequencing Kit (manufactured by Amersham Life Science), or (3) by BAS-2000 (manufactured by Fuji Film) using BcaBEST (trademark) Dideoxy Sequencing Kit (manufactured by TaKaRa). The total amino acid sequences of the protein (see SEQ ID NO: 2 and 4) were determined from the sequence (see SEQ ID NO: 1 and 3). The protein of the SEQ ID NO: 1 had 461 amino acids and its molecular weight was calculated to be 49564.15, and the protein of the SEQ ID NO: 2 had 551 amino acids and its molecular weight was calculated to be 58148.62, According to the present invention, it could be possible to provide a novel nicotianamine aminotransferase, a gene therefor and so on.

What is claimed is:

1. An isolated nucleic acid comprising:
   (a) a nucleotide sequence encoding an amino acid sequence represented by SEQ ID NO: 2 or 4, wherein said amino acid sequence having nicotianamine aminotransferase activity, or
   (b) a nucleotide sequence which hybridizes to the nucleotide sequence of SEQ ID NO: 1 or SEQ ID NO: 3 when incubated in a solution of 5× Denhart's solution, 5×SSPE and 0.1% SDS at 65° C. for 12 hours, washed once with 6×SSP at 65° C. for 10 minutes and washed twice with 2×SSP, 0.1% SDS at 42° C. for 10 minutes, and which comprises a DNA sequence that is amplifiable by polymerase chain reaction with the primers represented by SEQ ID NO: 5 and 6 repeating a cycle of incubation at 94° C. for 40 seconds, followed by 40° C. for 1 minute, and followed by 72° C. for 2 minutes 25 times, and then repeating a cycle of incubation at 94° C. for 40 seconds, followed by 45° C. for 1 minute, and followed by 72° C. for 2 minutes 25 times, wherein the coding sequence of said nucleotide sequence encodes an amino acid sequence having nicotianamine aminotransferase activity.

2. The isolated nucleic acid according to claim 1, which has a nucleotide sequence encoding the amino acid sequence represented by SEQ ID NO: 2 or 4.

3. The isolated nucleic acid according to claim 2, which has a nucleotide sequence represented by SEQ ID NO: 1 or 3.

4. A plasmid comprising a nucleic acid comprising:
   (a) a nucleotide sequence encoding an amino acid sequence represented by SEQ ID NO: 2 or 4, wherein said amino acid sequence having nicotianamine aminotransferase activity, or
   (b) a nucleotide sequence which hybridizes to the nucleotide sequence of SEQ ID NO: 1 or SEQ ID NO: 3 when incubated in a solution of 5× Denhart's solution, 5×SSPE and 0.11% SDS at 65° C. for 12 hours, washed once with 6×SSP at 65° C. for 10 minutes and washed twice with 2×SSP, 0.1% SDS at 42° C. for 10 minutes, and which comprises a DNA sequence that is amplifiable by polymerase chain reaction with the primers represented by SEQ ID NO: 5 and 6 repeating a cycle of incubation at 94° C. for 40 seconds, followed by 40° C. for 1 minute, and followed by 72° C. for 2 minutes 25 times, and then repeating a cycle of incubation at 94° C. for 40 seconds, followed by 45° C. for 1 minute, and followed by 72° C. for 2 minutes 25 times, wherein the coding sequence of said nucleotide sequence encodes an amino acid sequence having nicotianamine aminotransferase activity.

5. An expression plasmid comprising:
   (1) a promoter that functions in a host cell,
   (2) a nucleic acid comprising:
      (a) a nucleotide sequence encoding an amino acid sequence represented by SEQ ID NO: 2 or 4, wherein said amino acid sequence having nicotianamine aminotransferase activity, or
      (b) a nucleotide sequence which hybridizes to the nucleotide sequence of SEQ ID NO: 1 or SEQ ID NO: 3 when incubated in a solution of 5× Denhart's solution, 5×SSPE and 0.1% SDS at 65° C. for 12 hours, washed once with 6×SSP at 65° C. for 10 minutes and washed twice with 2×SSP, 0.1% SDS at 42° C. for 10 minutes, and which comprises a DNA sequence that is amplifiable by polymerase chain reaction with the primers represented by SEQ ID NO: 5 and 6 repeating a cycle of incubation at 94° C. for 40 seconds, followed by 40° C. for 1 minute, and followed by 72° C. for 2 minutes 25 times, and then repeating a cycle of incubation at 94° C. for 40 seconds, followed by 45° C. for 1 minute, and followed by 72° C. for 2 minutes 25 times, wherein the coding sequence of said nucleotide sequence encodes an amino acid sequence having nicotianamine aminotransferase activity, and (3) a terminator that functions in a host cell, wherein the promoter, the nucleic acid, and the terminator are operably linked in the above described order.

6. A process for constructing an expression plasmid, which comprises combining:

(1) a promoter that functions in a host cell, (2) a nucleic acid comprising;
   (a) a nucleotide sequence encoding an amino acid sequence represented by SEQ ID NO: 2 or 4, wherein said amino acid sequence having nicotianamine aminotransferase activity, or
   (b) a nucleotide sequence which hybridizes to the nucleotide sequence of SEQ ID NO: 1 or SEQ ID NO: 3 when incubated in a solution of 5× Denhart's solution, 5×SSPE and 0.1% SDS at 65° C. for 12 hours, washed once with 6×SSP at 65° C. for 10 minutes and washed twice with 2×SSP, 0.1% SDS at 42° C. for 10 minutes, and which comprises a DNA sequence that is amplifiable by polymerase chain reaction with the primers represented by SEQ ID NO: 5 and 6 repeating a cycle of incubation at 94° C. for 40 seconds, followed by 40° C. for 1 minute, and followed by 72° C. for 2 minutes 25 times, and then repeating a cycle of incubation at 94° C. for 40 seconds, followed by 45° C. for 1 minute, and followed by 72° C. for 2 minutes 25 times, wherein the coding sequence of said nucleotide sequence encodes an amino acid sequence having nicotianamine aminotransferase activity, and (3) a terminator that functions in a host cell, wherein the promoter, the nucleic acid, and the terminator are operably linked in the above described order, thereby generating an expression plasmid.

7. A host cell transformed with the plasmid as defined in claim 4 or 5.

8. The host cell according to claim 7, wherein the host cell is a microorganism.

9. The host cell according to claim 7, wherein the host cell is a plant cell.

10. A process for enhancing iron absorbing ability of a plant cell comprising introducing into a plant cell which absorbs iron using mugineic acid compound to solubilize the iron, an expression plasmid formed by combining:

(1) a promoter that functions in a host cell, (2) a nucleic acid comprising:
   (a) a nucleotide sequence encoding an amino acid sequence represented by SEQ ID NO: 2 or 4, wherein said amino acid sequence having nicotianamine aminotransferase activity, or
   (b) a nucleotide sequence which hybridizes to the nucleotide sequence of SEQ ID NO: 1 or SEQ ID NO: 3 when incubated in a solution of 5× Denhart's solution, 5×SSPE and 0.1% SDS at 65° C. for 12 hours, washed once with 6×SSP at 65° C. for 10 minutes and washed twice with 2×SSP, 0.1% SDS at 42° C. for 10 minutes, and which comprises a DNA sequence that is amplifiable by polymerase chain reaction with the primers represented by SEQ ID NO: 5 and 6 repeating a cycle of incubation at 94° C. for 40 seconds, followed by 40° C. for 1 minute, and followed by 72° C. for 2 minutes 25 times, and then repeating a cycle of incubation at 94° C. for 40 seconds, followed by 45° C. for 1 minute, and followed by 72° C. for 2 minutes 25 times, wherein the coding sequence of said nucleotide sequence encodes an amino acid sequence having nicotianamine aminotransferase activity, and (3) a terminator that functions in a host cell, wherein the promoter, the nucleic acid, and the terminator are operably linked in the above described order, and expressing said nucleic acid, wherein expression of said nucleic acid hi the plant cell enhances iron absorbing ability of the plant cell.

11. The process according to claim 10, wherein the nucleic acid comprises a nucleotide sequence encoding an amino acid sequence represented by SEQ ID NO: 2 or 4.

12. The plasmid according to claim 4, which comprises a nucleic acid comprising a nucleotide sequence encoding an amino acid sequence represented by SEQ ID NO: 2 or 4.

13. The expression plasmid according to claim 5, which comprises a nucleic acid comprising a nucleotide sequence encoding an amino acid sequence represented by SEQ ID NO: 2 or 4.

14. The process according to claim 6, wherein the expression plasmid comprises a nucleic acid comprising a nucleotide sequence encoding an amino acid sequence represented by SEQ ID NO: 2 or 4.

15. An isolated nucleic acid comprising:
   (a) a nucleotide sequence encoding an amino acid sequence represented by SEQ ID NO: 2 or 4, wherein said amino acid sequence having nicotianamine aminotransferase activity, or
   (b) a nucleotide sequence from barley, said nucleotide sequence hybridizes to the nucleotide sequence represented by SEQ ID NO: 1 or 3 when incubated in a solution of 5× Denhart's solution, 5×SSPE and 0.1% SDS at 65° C. for 12 hours, washed once with 6×SSP at 65° C. for 10 minutes and washed twice with 2×SSP, 0.1% SDS at 42° C. for 10 minutes, and wherein said nucleotide sequence encodes an amino acid sequence having nicotianamine aminotransferase activity.

* * * * *